(12) United States Patent
Douglass

(10) Patent No.: US 9,760,681 B2
(45) Date of Patent: Sep. 12, 2017

(54) OFFLINE ELECTRONIC HEALTH RECORD MANAGEMENT

(71) Applicant: PRACTICE FUSION, INC., San Francisco, CA (US)

(72) Inventor: Matthew Christopher Douglass, San Francisco, CA (US)

(73) Assignee: Practice Fusion, Inc., San Francisco, CA (US)

( * ) Notice: Subject to any disclaimer, the term of this patent is extended or adjusted under 35 U.S.C. 154(b) by 501 days.

(21) Appl. No.: 14/552,225

(22) Filed: Nov. 24, 2014

(65) Prior Publication Data

US 2016/0147944 A1 May 26, 2016

(51) Int. Cl.
| | |
|---|---|
| G06Q 10/00 | (2012.01) |
| G06Q 50/00 | (2012.01) |
| G06F 21/00 | (2013.01) |
| G06Q 20/00 | (2012.01) |
| G06F 19/00 | (2011.01) |
| G06F 21/31 | (2013.01) |
| H04L 9/08 | (2006.01) |
| G06F 21/62 | (2013.01) |

(52) U.S. Cl.
CPC ............ *G06F 19/322* (2013.01); *G06F 21/31* (2013.01); *G06F 21/6245* (2013.01); *H04L 9/0866* (2013.01); *G06Q 2220/10* (2013.01)

(58) Field of Classification Search
USPC ...................................... 705/2, 3, 50, 51, 64
See application file for complete search history.

(56) References Cited

U.S. PATENT DOCUMENTS 7,730,155 B1 * 6/2010 Meyer .................... H04W 4/02
709/201
8,601,475 B2 * 12/2013 Landsman ........ G06F 17/30899
718/100

(Continued)

OTHER PUBLICATIONS

U.S. Appl. No. 14/318,492, Douglass, M., "Medical Professional Application Integration into Electronic Health Record System," filed Jun. 27, 2014 (Not Published).

*Primary Examiner* — Robert Morgan
*Assistant Examiner* — Joshua Blanchette
(74) *Attorney, Agent, or Firm* — Sterne, Kessler, Goldstein & Fox P.L.L.C.

(57) ABSTRACT

Embodiments include an offline application, encrypted patient medical data records, and an encryption key that are stored in a cache of a browser application on the local computing device when a network connection is available. The offline application is accessed when the network connection is subsequently lost. Embodiments allow the user to access decrypted patient medical data records stored in the browser application cache, as well as create and access new patient medical data records when a network connection is offline. Any access to a patient medical data record when the network connection is offline may be documented in an offline-access record, an audit record that satisfies HIPAA Security Rule restrictions, that is created and encrypted. When a network connection becomes available, corresponding patient medical data records in the EHR system are updated or created according to the offline-access record and/or an offline-updated patient medical data record.

20 Claims, 6 Drawing Sheets

(56) References Cited

U.S. PATENT DOCUMENTS

| | | | | |
|---|---|---|---|---|
| 2002/0016911 A1* | 2/2002 | Chawla | ............ | G06F 17/30902 |
| | | | | 713/153 |
| 2009/0249076 A1* | 10/2009 | Reed | ............ | G06Q 30/00 |
| | | | | 713/181 |
| 2011/0087603 A1* | 4/2011 | Garcia | ............ | G06F 17/30905 |
| | | | | 705/55 |
| 2012/0185505 A1* | 7/2012 | Borden | ............ | G06F 17/30097 |
| | | | | 707/769 |
| 2012/0278093 A1* | 11/2012 | Amundson | ............ | G06Q 40/08 |
| | | | | 705/2 |
| 2013/0305039 A1* | 11/2013 | Gauda | ............ | G06F 21/6218 |
| | | | | 713/153 |

* cited by examiner

FIG. 6

OFFLINE ELECTRONIC HEALTH RECORD MANAGEMENT

BACKGROUND

Field

This field is generally related to managing an electronic health record offline, for example, when a network connection is not available.

Background

Electronic Health Records

Medical records related to a patient's health information are essential to the practice of medical care. Traditionally, medical records were paper-based documents. The emergence of electronic medical records (EMRs), which are a digital version of the paper chart that contains all of a patient's medical history from one medical practice, offers medical professionals and patients with new functionalities and efficiencies that paper-based medical records cannot provide. An EMR which can be incorporated into an electronic health record (EHR), is a collection of electronically stored information about an individual patient's medical history. EHRs may contain a broad range of data, including demographics, medical history, medication history, allergies, immunization records, laboratory test results, radiology images, vital signs, personal statistics like age and weight, and billing information. Many commercial EHR systems combine data from a number of healthcare services and providers, such as clinical care facilities, laboratories, radiology centers, and pharmacies.

EHRs are a drastic improvement over paper-based medical records. Paper-based medical records require a large amount of physical storage space. Paper records are often stored in different locations, and different medical professionals may each have different and incomplete records about the same patient. Obtaining paper records from multiple locations for review by a healthcare provider can be time consuming, complicated, and sometimes impossible. In contrast, EHR data is stored in digital format, and thus are more secure and can be accessed from anywhere. EHR systems significantly simplify the reviewing process for healthcare providers. Because records in EHRs can be linked together, EHRs vastly improve the accessibility of health records and the coordination of medical care.

EHRs also decrease the risk of misreading errors by healthcare professionals. Poor legibility is often associated with handwritten, paper medical records, which can lead to medical errors. EHRs, on the other hand, are inherently legible given that they are typically stored in typeface. In addition, EHRs enhance the standardization of forms, terminology and abbreviations, and data input, which help ensure reliability of medical records, and standardization of codesets and storage of EHR data means that data from different technical information systems can be displayed in a single, unified record. Further, EHRs can be transferred electronically, thus reducing delays and errors in recording prescriptions or communicating laboratory test results.

The benefits of digitizing health records are substantial. Healthcare providers with EHR systems have reported better outcomes, fewer complications, lower costs, and fewer malpractice claim payments. But despite EHRs' potential in drastically improving the quality of medical care, only a low percentage of healthcare providers use EHR systems. While the advantages of EHRs are significant, they also carry concerns, including high costs, lost productivity during EHR system implementation or computer downtime, and lack of EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as health information doctors and nurses input, documented conversations between a doctor and a patient, and information use to process or facilitate medical billing claims and documents. The HIPAA Security Rule, effective on Apr. 20, 2005 for most covered entities, adds additional constraints to electronic data security and the storage and transmission of PHI.

The high cost of EHR systems also significantly hinders EHR adoption. A large number of physicians without EHR systems have referred to initial capital costs as a barrier to adopting EHR systems. Cost concerns are even more severe in smaller healthcare settings, because current EHR systems are more likely to provide cost savings for large integrated institutions than for small physician offices. During the EHR system technology's setup and implementation process, productivity loss can further offset efficiency gains. The need to increase the size of information technology staff to maintain the system adds even more costs to EHR system usages.

Usability is another major factor that holds back adoption of EHR systems. It is particularly challenging to develop user-friendly EHR systems. There is a wide range of data that needs to be integrated and connected. Complex information and analysis needs vary from setting to setting, among healthcare provider groups, and from function to function within a healthcare provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHR systems in revolutionizing the healthcare system, calls for better EHR systems that are secure, cost-effective, efficient, and user-friendly.

Comprehensive EHR systems can provide capabilities far beyond simply storing patients' medical records. Because EHR systems offer healthcare providers and their workforce members the ability to securely store and utilize structured health information, EHR systems can have a profound impact on the quality of the healthcare system. In Framework for Strategic Action on Health Information Technology, published on Jul. 21, 2004, the Department of Health & Human Services (HHS) outlined many purposes for EHR services. The outlined purposes include, among other things, improving healthcare outcomes and reducing costs, reducing recordkeeping and duplication burdens, improving resource utilization, care coordination, active quality and health status monitoring, reducing treatment variability, and promoting patients' engagement in and ownership over their own healthcare.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for healthcare providers to adopt and meaningfully use EHR systems in their practices. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

Losing a Network Connection

When a healthcare provider uses a computing device to access an electronic health record (EHR) system and a network connection is lost, the healthcare provider typically has no access to patient medical data records while offline. Yet medical records access may be critically important to a healthcare provider's practice. For example, the inability of a healthcare provider to research a patient's medical data record when the patient is experiencing an on-going problem in a hospital significantly impairs the healthcare provider's ability to make crucial medical decisions.

BRIEF SUMMARY

In addition to the inability to access patient medical data records when a network connection is lost, the HIPAA Security Rule introduces restrictions on disclosure of and access to protected health information. Embodiments include a technical solution that includes transforming and storing patient medical data records in the cache of a browser to enable access to patient medical data records even when network connection to an EHR system is lost, as well as creating and transforming audit records that satisfy HIPAA Security Rule restrictions.

Embodiments avoid a user having to install or configure a backup system associated with the EHR system. In an embodiment, patient medical data records that the user may access are transformed, (e.g., encrypted), and stored along with an offline application in a browser application cache on the local computing device when a network connection is available. Later, when a network connection is lost or offline, the offline application may be accessed. Embodiments further include authenticating the user, and when the user is authenticated, generating an offline encryption key with the authentication data to decrypt the encrypted patient medical data records in the local cache, and allowing the user to access the decrypted patient medical data records, as well as to create new patient medical data records. The access may include selecting, viewing, or updating (e.g., modifying and/or deleting) a decrypted or new patient medical data record. In addition, an audit record of patient medical data records that are accessed while the network connection is offline, is created and encrypted to satisfy HIPAA Security Rule restrictions. Once a network connection becomes available, the EHR system initiates updates to older patient medical data records in the EHR system associated with offline-updated patient medical data records (e.g., the decrypted patient medical data records that were updated while offline, or patient medical data records that were created while offline including any updates); the EHR system also receives offline-access records (e.g., audit records that document: access to any decrypted patient medical data records while the network connection is offline, and the creation of and access to any new patient medical data records while the network connection is offline).

Embodiments include a method, program storage device, and a system for offline electronic health record (EHR) management by a client device, when a network connection is offline. Embodiments include accessing an offline application in a browser application cache, presenting an offline-login to an EHR system to a user through the browser application, receiving login credentials from the user, authenticating the login credentials, and when the login credentials are authentic, generating an offline encryption key based on the login credentials; embodiments farther include comparing the offline encryption key to an encryption key stored in the browser application cache. When the offline encryption key matches the encryption key, embodiments further include accessing an encrypted patient medical data record in a plurality of encrypted patient medical data records stored in the browser application cache, decrypting the encrypted patient medical data record with the offline encryption key, and creating an offline-updated patient medical data record based on the decrypted patient medical data record. In addition, embodiments include creating an offline-access record based on the offline-updated patient medical data record, and encrypting and storing each of the offline-updated patient medical data record and the offline-access record locally in the browser application cache.

When the network connection is available, embodiments include the client device receiving from a server, a request for an offline-access record and an offline-updated patient medical data record, and transmitting to the server, the encrypted offline-access record and the encrypted offline-updated patient medical data record from the browser application cache, where a corresponding patient medical data record stored at the server is updated with information contained in the offline-updated patient medical data record and the encrypted offline-access record.

Further embodiments, features, and advantages, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable one of ordinary skill in the art to make and use the disclosure.

FIG. 6 illustrates an example interface that presents a patient medical data record.

The drawing in which an element first appears is typically indicated by the leftmost digit or digits in the corresponding reference number. In the drawings, like reference numbers may indicate identical or functionally similar elements.

DETAILED DESCRIPTION

Overview

Figure 1:
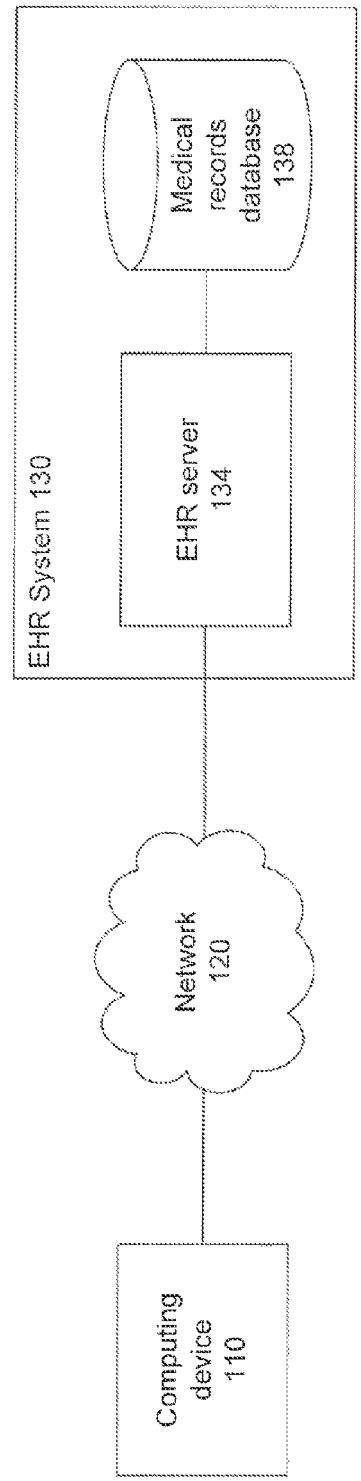
FIG. 1 is a diagram illustrating an example system for managing an electronic health record offline, according to an embodiment.

When a user makes medical decisions regarding a patient's diagnosis or treatment, the user typically accesses the patient's medical data record in an EHR system. The user may use a computing device that communicates over a network connection to an EHR system. The computing device may be, for example and without limitation, a smart phone, a tablet, a personal digital assistant (PDA), or a personal computer, For example, the user may use the computing device to obtain, view, modify, and/or delete a patient medical data record, or create a new patient medical data record.

When the network connection is lost, the user typically loses access to patient medical data records. The network connection may be lost for various reasons. For example, the user's computing device may move out of a wireless service range, the user may disconnect a browser application on the computing device from the Internet, the user may restart the computing device or the browser application, the physical network connection may be disconnected or unavailable, or an EHR server in the EHR system may be out of service (e.g., for maintenance reasons or an unscheduled outage). When the network connection is lost, the user is typically unable to access patient medical data records. This may significantly impair the user's ability to make crucial life-saving medical decisions.

Figure 6:
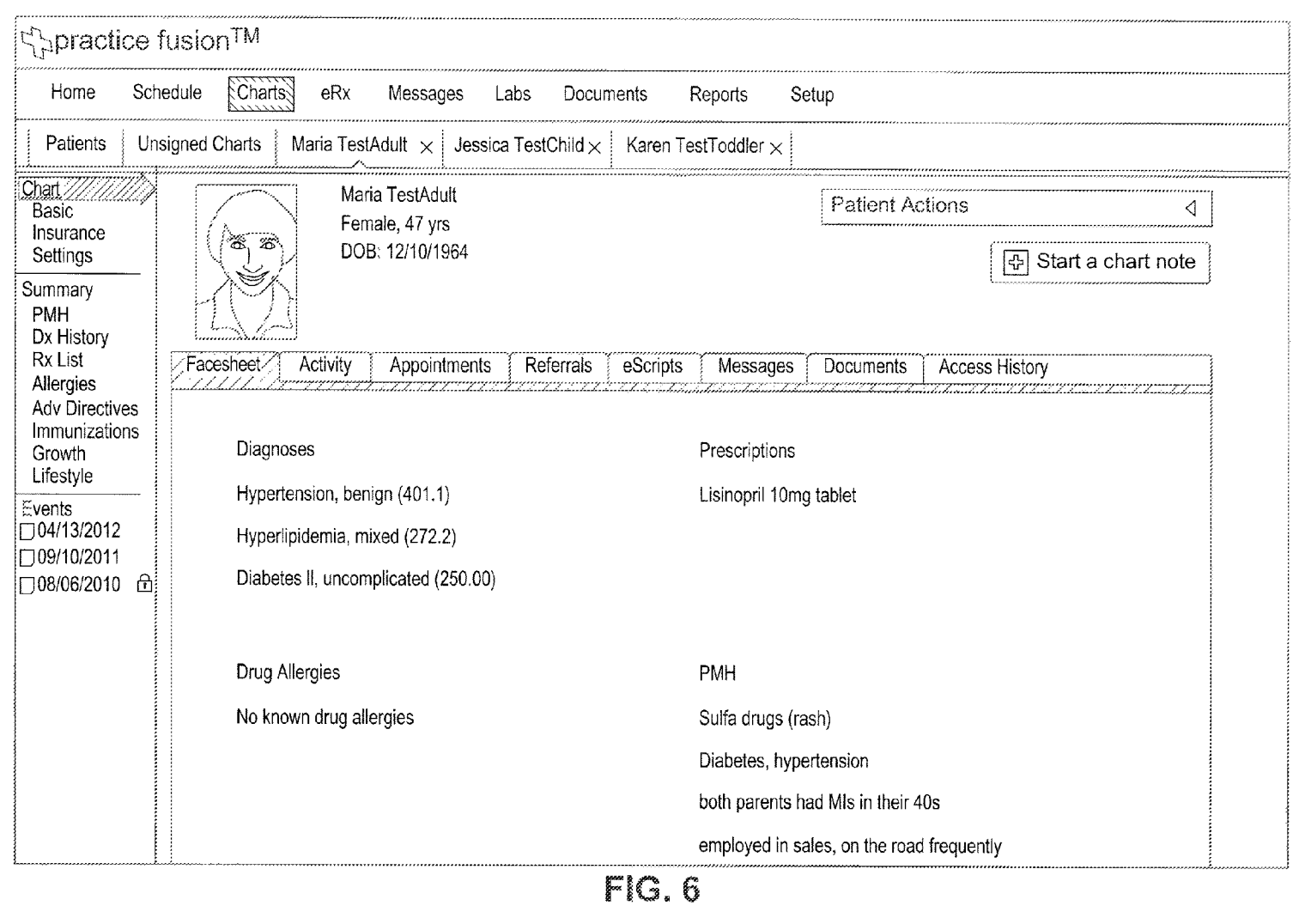

Embodiments allow a user (e.g., a health care provider such as a physician or a nurse) to access patient medical data records of an EHR system even when the network connection is disabled or unavailable. When a patient visits a healthcare provider, the provider typically reviews a patient medical record using the EHR system. FIG. 6 illustrates an example interface that presents a patient medical data record. The patient medical data record contains various types of information about a particular patient, from basic facts to more detailed medical information. Disparate types of information may be separated into various tabs, as illustrated in FIG. 6. For example, FIG. 6 has a home screen for the patient that includes tabs for "messages" and "documents." There is also a "Start a chart note" button that may be selected when a healthcare provider wishes to add new information into the record. The patient medical data record typically includes data associated with a patient including, for example and without limitation, medical data, billing data, insurance data, appointment data, and/or demographic data.

In embodiments, encrypted patient medical data records, an offline application, and an encryption key may be stored in a browser application cache on the local computing device when a network connection is available. The offline application is accessed when the network connection is subsequently lost. The encryption key may be used to determine if the user is authorized to access the encrypted patient medical data records. When the user is an authorized user, the offline application transforms (i.e., decrypts) the encrypted patient medical data records stored in the browser application cache, and allows the user to access (e.g., select, view and/or update) the decrypted patient medical data records. The combination of the encrypted patient medical data records, offline application, and the encryption key being stored in the browser application cache is a technical improvement over prior methods that avoids a user having to install or configure a backup system associated with the EHR system, and enables embodiments that satisfy HIPAA Security Rule restrictions.

The offline application may also allow the user to create and access (e.g., select, view and/or update) new patient medical data records. Updating a patient medical data record may include modifying and/or deleting the patient medical data record. A decrypted patient medical data record that is updated when a network connection is offline, or a patient medical data record that is created and updated when a network connection is offline will be referred to herein as an offline-updated patient medical data record. For example, a user may be examining a new patient when a network connection is lost. The user may continue the examination and create a new patient medical data record for that patient, which will be stored as an offline-updated patient medical data record. Offline-updated patient medical data records are encrypted and stored in a local memory.

Any access to a decrypted patient medical data record or a patient medical data record created when the network connection is offline may be documented in conformance with HIPAA Security Rules. For example, the offline application may store such access in an offline-access record. Data documenting the access may include, for example and without limitation, the type of patient medical data record access (e.g., selecting, viewing, creating, modifying, and/or deleting), information identifying the patient medical data record accessed, an identification of the user who accessed the patient medical data record, a date and time of access, and/or the content added, modified, or deleted during the access. Offline-access records and offline-updated patient medical data records are encrypted and stored in a local memory. When a network connection becomes available, the offline-access records and/or offline-updated patient medical data records are uploaded to the EHR system; corresponding older patient medical data records are updated accordingly or new patient medical data records are established accordingly.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

System

FIG. 1 is a diagram illustrating an example system 100 for managing an electronic health record offline, according to an embodiment. System 100 includes a computing device 110 and an EHR system 130 connected by one or more networks 120, such as the Internet. EHR system 130 includes at least EHR server 134 and medical records database 138.

Computing device 110 may be any type of computing device, such as, for example and without limitation, a personal computer, a mobile phone, a tablet, a PDA, a workstation, an embedded system, a game console, a television, a set top box, or the like. Computing device 110 may, for example, include a web browser application that enables a user to log into an EHR system. The web browser application responds to user input, such as a user selection on an EHR interface, by sending an hypertext transfer protocol (HTTP) request to EHR server 134 in EHR system 130 via network 120. In an embodiment, the web browser application is an HTML-5 compliant browser application.

EHR system 130 includes at least EHR server 134 coupled to a medical records database 138. EHR server 134 may be implemented on one or more computing devices having server capabilities. Such a computing device may include, but is not limited to, a device having a processor and memory, including a non-transitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm. An example of establishing communications between a computing device and an EHR system is in U.S. patent application Ser. No. 14/318,492, filed on Jun. 27, 2014, entitled Medical Professional Application Integration into Electronic Health Record System, which is incorporated herein by reference in its entirety.

Medical records database 138 may be any type of structured data store, including a relational database.

Method

To manage patient records when a network connection to is offline, computing device 110 and EHR system 130 may operate as described below with respect to FIGS. 2-4. For ease of discussion and without limitation, methods 200, 300, and 400 are described with reference to elements from FIG. 1.

Figure 2:
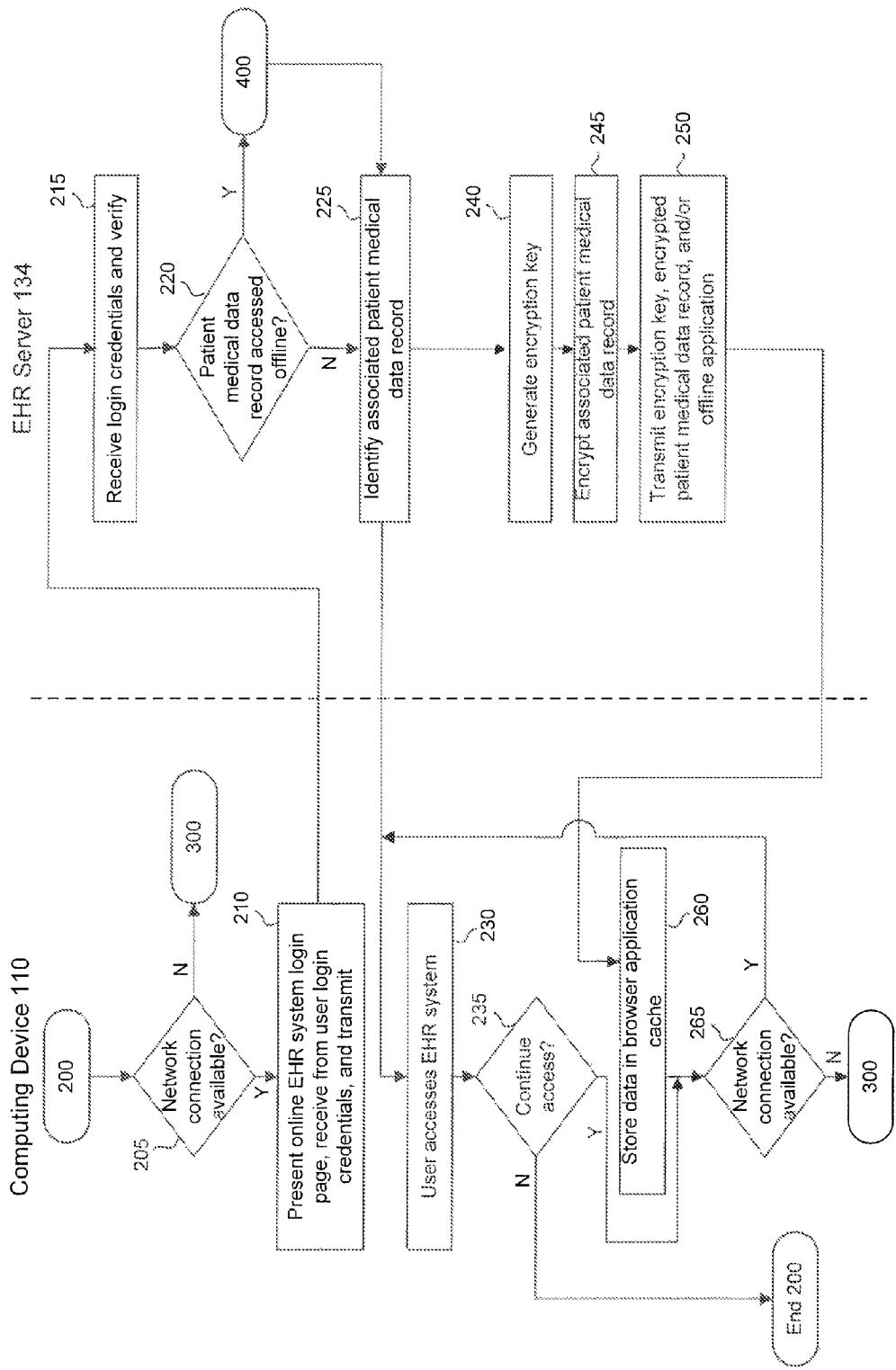
FIG. 2 is a flowchart illustrating an example method for managing an electronic health record offline, according to an embodiment.

FIG. 2 is a flowchart illustrating an example method 200 for managing an electronic health record offline, according to an embodiment. Method 200 begins at step 205, where a determination is made regarding whether a network connection is available. If a network connection is not available, method 200 proceeds to method 300 (described with respect to FIG. 3, below). When a network connection is available, method 200 proceeds to step 210.

At step 210, computing device 110 presents an online EHR system login to a user. The system login may be found, for example, on a home page of EHR system 130. Computing device 110 receives login credentials from the user and transmits the login credentials to EHR server 134. The login credentials may include, for example, a username and a password.

At step 215, EHR server 134 receives the user's login credentials and verifies that the user is authorized to access EHR system 130. The verification may include comparing the login credentials to data in a security database, for example. When the user is verified and authorized, method 215 proceeds to step 220. When the user cannot be verified and/or authorized, method 200 ends.

At step 220, a determination is made whether the user has accessed a patient medical data record while offline. For example, an indicator may have been transmitted from computing device 110, such as with the user's login credentials, that indicates whether the user has or has not accessed a patient medical data record while offline. In an embodiment, the indicator includes the identity of computing device 110. When a user has accessed a patient medical data record while the network connection was offline, method 200 proceeds to method 400. When the user has not accessed a patient medical data record while offline, method 200 proceeds to step 225. For example, when the user logs onto EHR system 130 for the first time, the user has not yet experienced an offline situation.

At step 225, patient medical data records associated with the user are identified. For example, EHR server 134 may identify and retrieve patient medical data records from medical records database 138 based on at least one of: the user's electronic appointment schedule (e.g., patient medical data records of patients scheduled for today and tomorrow), the age of patients associated with the user (e.g., oldest and/or youngest patients), an indicator of the patients likely needing immediate attention (e.g., sickest patients, patients undergoing critical treatments, most likely patients to be hospitalized), demographics (e.g., patients associated with a particular office or hospital), a filter on a field of a patient medical data record, a combination of these, or all of the patient medical data records associated with the user. Patient medical data records may also be identified based on a specific request for a particular patient medical data record from the user. Once the patient medical data records and/or sections of patient medical data records are identified, method 200 continues to steps 230 and 240. Step 230 involves normal, online patient medical data records access; step 240 involves preparation for offline access.

At step 230, the user accesses a patient medical data record and/or a section of a patient medical data record identified in EHR system 130 as being associated with the user. The user may view, modify, and/or delete the patient medical data record. In addition, the user may create a new patient medical data record, for example, for a new patient.

In an embodiment, the user may request a patient medical data record by entering patient data. Patient data may include but is not limited to: a last name, a first name, a birth date, a social security number, an insurance policy number, an identifier that uniquely identifies the patient medical data record, and the like. As part of the user access, computing device 110 may transmit the request, including the patient data, to EHR server 134. EHR server 134 may obtain the requested patient medical data record from medical records database 138 based on the patient data, and transmit the patient medical data record to computing device 110.

At step 235, a determination is made whether the user wants to continue to access EHR server 134. When the user does not want to continue access, method 200 ends. When the wants to continue to access EHR server 134, method 200 continues to step 265.

Returning to step 240 to prepare for offline access, EHR server 134 obtains an encryption key associated with the user. The encryption key may be generated in real time based on the user's login credentials. For example, a user's login credentials may include a username and a password that may be hashed to generate the encryption key. Or, the username and/or password may be used to generate a salt as part of the encryption key, as would be understood by one of ordinary skill in the art. Encryption mechanisms may be isolated to a javascript file, for example, and may be generated in accordance with, for example, the American Encryption Standard (AES) or a blowfish-type cipher. Alternatively, the obtained encryption key may be a previously-generated encrypted key.

At step 245, EHR server 134 encrypts the patient medical data records identified in step 225. In an embodiment, only selected data are encrypted and stored in the browser application cache on computing device 110. For example, if low memory is a limitation on computing device 110, then a subset of the patient medical data records identified may be selected and encrypted, or certain sections of the identified patient medical data records may be selected and encrypted. In another example, certain sections of all patient medical data records may be selected, identified and retrieved (e.g., by filtering as described above at step 225), then encrypted at step 245 to conserve limited memory on computing device 110. In an embodiment, the one or more combinations of selected data associated with the identified patient medical data records (e.g., a filtered subset of a corpus of patient medical data records associated with the user) are symmetrically encrypted with the encryption key, and are referred to as encrypted patient medical data records.

At step 250, EHR server 134 transmits at least one of the following, which may be stored in a browser application cache of local computing device 110: the encryption key, the encrypted patient medical data records, and an offline application. In an embodiment, the offline application is a thick client application. The thick client application may, for example, include an application framework, and may be accessed by the browser application on computing device 110 when a network connection is unavailable or offline. The offline application may manage patient medical data records without a continuous network connection to EHR server 134, but will need occasional access to EHR server 134. In an embodiment, EHR server 134 stores at least one of the encryption key, the encrypted patient medical data records, and the offline application in a file, which may then be transmitted to a browser application cache. In an embodiment, the offline application is transmitted to computing device 110 only once, though the offline application software may be updated as needed by EHR server 134. At least one of the encryption key and the encrypted patient medical data records is transmitted intermittently, periodically, according to a schedule, after an update or change occurs to a patient medical data record associated with the user, or combination thereof. For example, updated information may be sent periodically to computing device 110 after a change to the encryption key or an update to a patient medical data record associated with the user. The user's electronic appointment schedule may also be encrypted and transmitted to the computing device 110.

At step 260, computing device 110 receives and stores at least one of the following into the browser application cache of computing device 110: the encryption key, the encrypted patient medical data records, the offline application, and the encrypted electronic appointment schedule of the user. An HTML-5 compliant browser application may store static web pages in a browser cache. However, embodiments of the present invention also include storing the combination of the encryption key, the encrypted patient medical data records, the offline application, and/or the encrypted electronic appointment schedule in the browser application cache. The embodiments provide technical advantages that avoids a user having to install or configure a backup system associated with the EHR system, authenticates a user when the network is offline, and when a user is authenticated, generates an offline encryption key with the authentication data to decrypt the encrypted patient medical data records, and allows embodiments to satisfy HIPAA Security Rule restrictions. Computing device 110 may also receive updates intermittently, periodically, according to a schedule, or a combination thereof.

At step 265, a determination is made whether a network connection is still available. When a network connection is available, method 200 returns to step 230. When a network connection is not available, method 200 proceeds to method 300.

Figure 3:
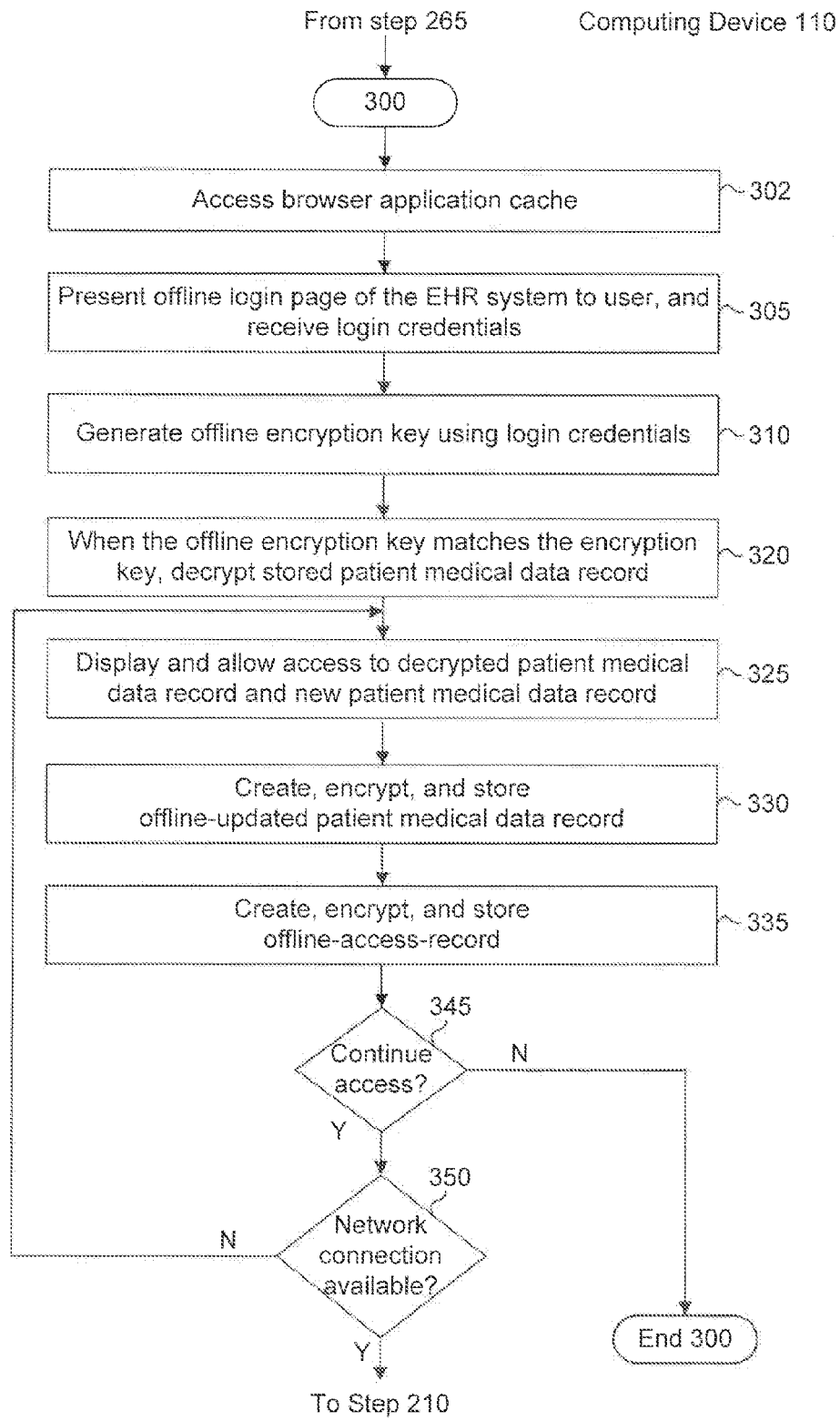
FIG. 3 is a flowchart illustrating more details of an example method for managing an electronic health record offline, according to an embodiment.

FIG. 3 is a flowchart illustrating more details of an example method 300 for managing an electronic health record offline, according to an embodiment. Method 300 begins at step 302, where computing device 110 accesses the browser application cache and loads the offline application. In an embodiment, the offline application may remain resident in the browser application when the browser application is closed or when computing device 110 is restarted. If an offline application is not present in the browser application cache, method 300 returns to step 205.

At step 305, computing device 110 presents a user with an offline login page to access the encrypted patient medical data records from EHR system 130, and receives login credentials from the user.

At step 310, computing device 110 generates an offline encryption key based on the login credentials received from the user. For example, a user's login credentials may include a username and a password that may be hashed to generate an offline encryption key. Or, the username and/or password may also be used to generate a salt as part of the offline encryption key as would be understood by one of ordinary skill in the art. Encryption mechanisms may be isolated to a javascript file, for example, and may be generated in accordance with, for example, the American Encryption Standard (AES) or a blowfish-type cipher.

The encryption key stored in the browser application cache may be used to confirm that the user is authorized to access the encrypted patient medical data records in the browser application cache. At step 320, computing device 110 compares the offline encryption key to the encryption key stored in the browser application cache; when the offline encryption key matches the stored encryption key, the computing device 110 may use the offline encryption key to transform the encrypted patient medical data records stored in the browser application cache (e.g., decrypt the encrypted patient medical data records). In an embodiment, the user's electronic appointment schedule may also be decrypted with the offline encryption key. If the offline encryption key does not match the stored encryption key, the user is not authorized to access the encrypted patient medical data records, and method 300 ends.

At step 325, computing device 110 displays a decrypted patient medical data record or a new patient medical data record created while the network connection is offline, for example, on a device screen or a monitor. The user may access (e.g., select, view, and/or update) the decrypted or newly created patient medical data record as she normally would when the network connection is available to EHR system 130. For example, the user may update (e.g., modify or delete) a decrypted or created patient medical data record.

In an embodiment, the user may access a decrypted patient medical data record based on at least one of: the user's electronic appointment schedule (e.g., decrypted patient medical data records of patient(s) scheduled for appointments within an hour of the current date and time), or a field in the patient medical data record (e.g., by searching for a decrypted patient medical data record based on one or more fields in a patient medical data record). For example, the user may request a decrypted patient medical data record by entering patient data. Patient data may include, but is not limited to, a last name, a first name, a birth date, a social security number, an insurance policy number, an identifier that uniquely identifies the patient medical data record, and the like. Computing device 110 may obtain the patient's decrypted patient medical data record from among the plurality of decrypted patient medical data records. In an embodiment, the user may access a patient medical data record created while the network connection is offline based on a field in the patient medical data record by entering patient data as described above. Computing device 110 may obtain the patient medical data record from among the plurality of patient medical data records created while the network connection is offline.

At step 330, computing device 110 may create, encrypt, and store an offline-updated patient medical data record. An offline-updated patient medical data record is created when an update to a decrypted patient medical data record or a newly created patient medical data record is made. As an example, an offline-updated patient medical data record may include detailed patient access history, new patient records, or detailed changes regarding prescribed medications, orders, notes, billing information, appointment schedules, or any other fields in a decrypted patient medical data record. A newly created patient medical data record may also be considered an offline-updated patient medical data record. In an embodiment, computing device 110 symmetrically encrypts an offline-updated patient medical data record with the offline encryption key, and stores the encrypted offline-updated patient medical data record in a local memory.

At step 335, computing device 110 creates, encrypts, and stores an offline-access record of the user's access (e.g., selecting, viewing, or updating) of any decrypted patient medical data records, and the creation and access of any new patient medical records. For example, when the user views a decrypted patient medical data record, the access is recorded, even when updates (e.g., modifications and/or deletions) are not made. Information in an offline-access record may include, for example and without limitation, at least one of the following: information that identifies the patient associated with an accessed patient medical data record (e.g., a decrypted or new patient medical data record that has been viewed); information that identifies the accessed patient medical data record; and/or any offline-updated patient medical data records associated with the decrypted or new patient medical data record. The offline-access record may also be transformed, (e.g., encrypted), for example, symmetrically encrypted with the offline encryption key, and stored in a local memory. Alternatively, the encrypted offline-access record may be stored in the browser application cache. In an embodiment, the offline-access record is part of an offline-updated EHR.

At step 345, a determination is made regarding whether the user wants to continue to access patient medical data records, e.g., a decrypted patient medical data record or a new patient medical data record. When the user does not want to continue, method 300 ends. When the user wants to continue, method 200 continues to step 350.

At step 350, a determination is made regarding whether a network connection is available. When a network connection is available, method 300 returns to step 210 as described above to access EHR system 130. When a network connection is still not available, method 300 returns to step 325.

Figure 4:
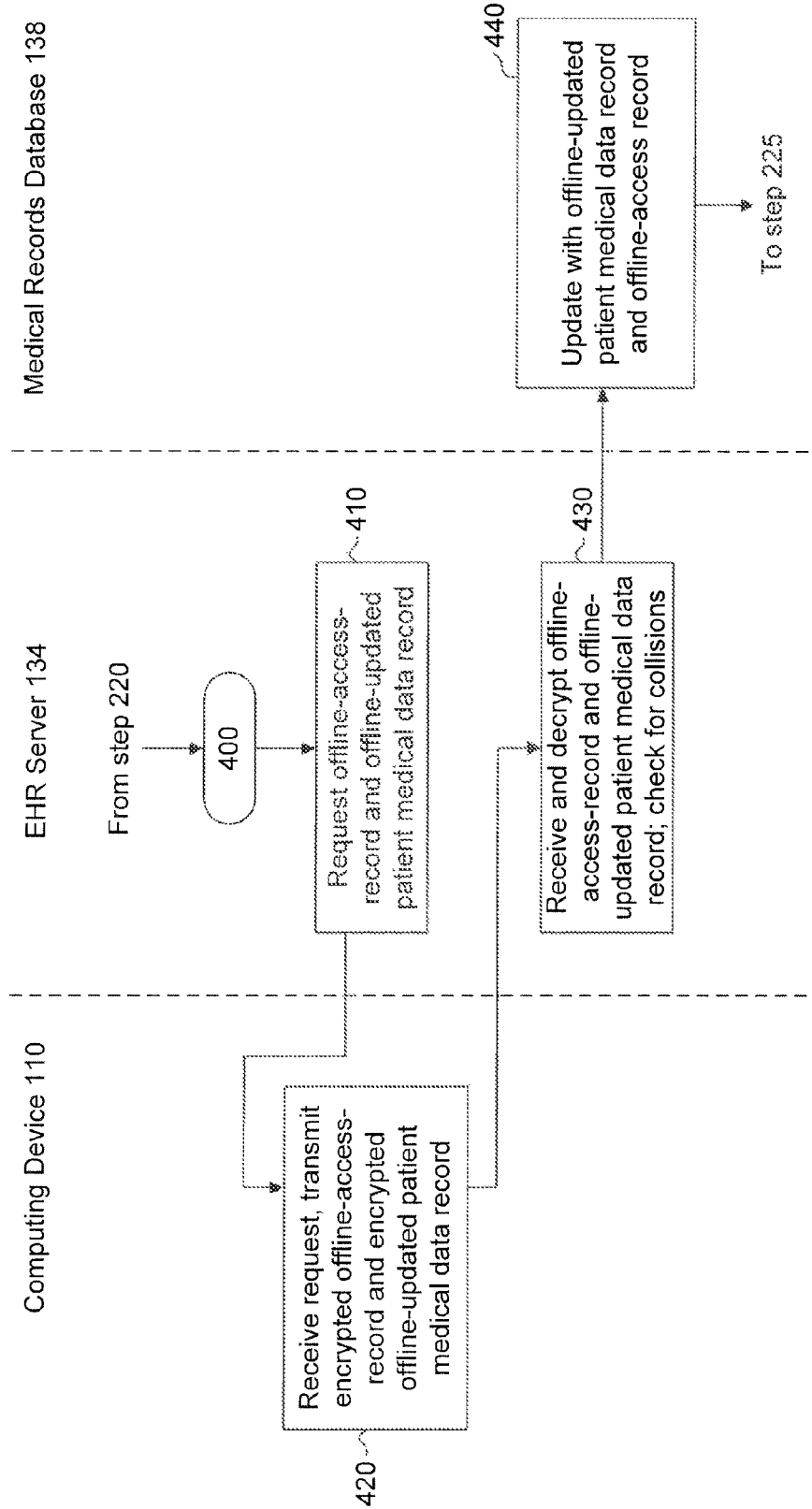
FIG. 4 is another flowchart illustrating more details of an example method for managing an electronic health record offline, according to an embodiment.

FIG. 4 is another flowchart illustrating details of an example method 400 for managing an electronic health record offline, according to an embodiment. Method 400 describes how offline-updated patient medical data records are synched back to EHR system 130. Method 400 begins at step 410, where EHR server 134 transmits a request to computing device 110 for any offline-access records and an offline-updated patient medical data records. For example, EHR server 134 may include mechanisms such as WebSockets, Server Events, Long Polling, and/or regular polling to assist in receiving an offline-updated patient medical data record (e.g., updated patient data) and/or offline access records.

At step 420, computing device 110 receives the request from EHR server 134. In response, computing device 110 transmits an encrypted offline-access record and an encrypted offline-updated patient medical data record to EHR server 134.

At step 430, EHR server 134 receives and decrypts the offline-access record and the offline-updated patient medical data record; the decryption may be performed with the encryption key generated at step 240, for example. Method 400 proceeds to step 440.

It is possible that a collision may occur when two or more computing devices send an offline-updated patient medical data record associated with the same patient to EHR server 134. For example, a doctor and a nurse from the same medical practice may each update a decrypted patient medical record associated with the same patient when the network connection is offline, and each of their computing devices will create an off-line updated patient medical data record for the same patient. Thus, more than one offline-updated patient medical data record corresponding to the same patient may be received by EHR server 134. In an embodiment, when a collision occurs for an offline-updated patient medical data record, EHR server 134, sends a notice to the computing device of the user responsible for the latest offline-updated patient medical data record (e.g., the nurse) or to a user with a higher priority (e.g., the doctor) to request a confirmation to proceed with updating the older version of patient medical data record in medical records database 138. The request for confirmation may include but is not limited to: a date and time each of the two or more offline-updated patient medical data records that have collided was created, the identity of the users making the updates, the patient associated with the two or more offline-updated patient medical data records, or the fields and field values updated. The user may respond to confirm or deny the request to proceed via the computing device to EHR server 134. EHR server 134 may update the associated patient medical data record accordingly.

At step 440, an older patient medical data record is updated with the offline-updated patient medical data record (e.g., modifications or deletions made to a decrypted patient medical data record) in medical records database 138. Alternatively, a new patient medical data record is established in medical records database 138 for the offline-updated patient medical data record that was created while the network connection was offline, and includes any updates made while offline.

In addition, a patient medical data record associated with the offline-access record is updated accordingly in medical records database 138, providing an audit record for the patient medical data record that was accessed while offline, thus satisfying HIPAA Security Rule restrictions.

Method 400 then proceeds to step 225.

Computing Device

Figure 5:
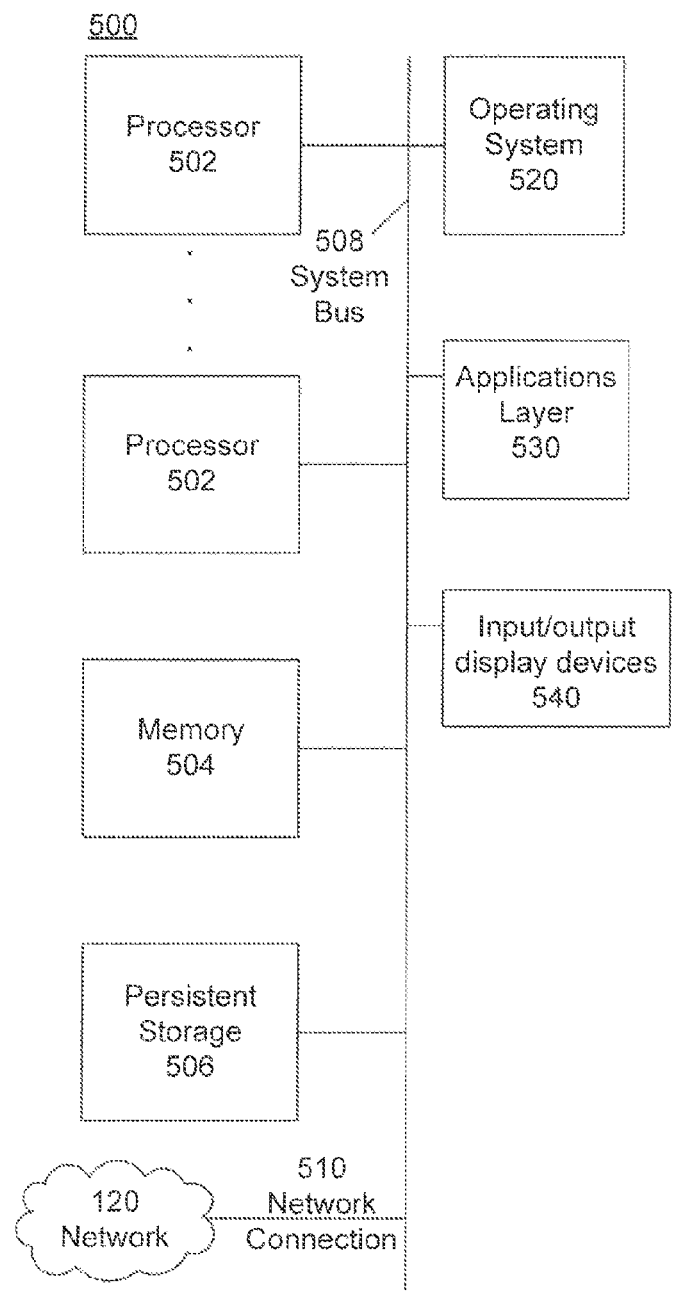
FIG. 5 is a diagram illustrating an example computing device, according to an embodiment.

An example computing device 500 is illustrated in FIG. 5. Computing device 500 accesses a network 220 over a network connection 510. Network connection 510 that provides computing device 500 with telecommunications capabilities. Computing device 500 uses an operating system 520 as software that manages hardware resources and coordinates the interface between hardware and software. Operating system 520 may include but is not limited to, for example, the iOS platform produced by Apple Inc. of Cupertino, Calif., the Android platform produced by Google Inc. of Mountain View, Calif., the Windows platform produced by Microsoft Corp. of Redmond, Wash., the Blackberry platform produced by Blackberry Ltd. of Ontario, Calif., or the open-source Linux platform.

In an embodiment, computing device 500 contains a combination of hardware, software, and firmware constituent parts that allow it to run an applications layer 530. Computing device 500, in embodiments, may be organized around a system bus 508, but any type of infrastructure that allows the hardware infrastructure elements of computing device 500 to communicate with and interact with each other may also be used.

Processing tasks in the embodiment of FIG. 5 are carried out by one or more processors 502. Processor 502 may include suitable logic, circuitry, dedicated circuits, and/or code that enables processing of data and/or controlling operations of computer system 500. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 502 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

To manipulate data in accordance with embodiments describe herein, processors 502 access a memory 504 via system bus 508. Memory 504 is non-transitory memory, such as random access memory (RAM). Memory 504 may include one or more levels of cache. Memory 504 has stored therein control logic (e.g., computer software) and/or data. For data that needs to be stored more permanently, processors 502 access persistent storage 504 via system bus 508. Persistent storage 506 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 502, memory 504, and persistent storage 506 cooperate with operating system 520 to provide basic functionality for computing device 500. Operating system 520 provides support functionality for applications layer 530.

Network connection 510 enables computer device 500 to communicate and interact with any combination of remote devices, remote networks, remote entities, etc. For example, network connection 510 may allow computer device 500 to communicate with remote devices over network 504, which may be a wired and/or wireless network, and which may include any combination of LANs, WANs, the Internet, etc. Control logic and/or data may be transmitted to and from computer device 500 via network connection 510.

Computing device 500 also includes input/output/display devices 540, such as a touchscreen, a camera/scanner, monitors, keyboards, pointing devices, Bluetooth devices, etc.

Applications layer 530 may house various components that perform methods 200-400 as described in FIGS. 2-4 when computing device 500 is used as computing device 110, or when computing device 500 is used as EHR server 134. In an embodiment, applications layer 530 houses the offline application.

It should be noted that computer-readable medium embodiments may include any physical medium which is capable of encoding instructions that may subsequently by used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

CONCLUSION

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for offline electronic health record (EHR) management, comprising:
   receiving by a client device, via a network connection, an encryption key and an encrypted patient medical data record corresponding to the encryption key;
   storing, by the client device, the encryption key and the encrypted patient medical data record in a browser application cache;

determining by the client device, that the network connection is offline;

by the client device, in response to the network connection being offline:
   accessing an application in the browser application cache;
   presenting, to a user, a login through the application;
   receiving login credentials from the user;
   generating an offline encryption key based on the login credentials;
   comparing the offline encryption key to the encryption key stored in the browser application cache;
   determining that the offline encryption key matches the encryption key; and
   in response to the offline encryption key matching the encryption key:
     accessing the encrypted patient medical data record stored in the browser application cache;
     decrypting the encrypted patient medical data record with the offline encryption key;
     creating an offline-updated patient medical data record based on the decrypted patient medical data record;
     creating an offline-access record based on the offline-updated patient medical data record; and
     encrypting and storing the offline-updated patient medical data record and the offline-access record locally in the browser application cache using the offline encryption key;

determining, by the client device, that the network connection is available; and by the client device, in response to the network connection being available:
   receiving, from a server, a request for an offline-access record and an offline-updated patient medical data record; and
   transmitting, to the server, the encrypted offline-access record and the encrypted offline-updated patient medical data record from the browser application cache.

2. The computer-implemented method of claim 1, further comprising, prior to the determining by the client device, that the network connection is offline:
receiving, from the server, the application; and
locally storing, by the client device, the received application in the browser application cache.

3. The computer-implemented method of claim 1, wherein the encrypted patient medical data record received from the server constitutes a filtered subset of a corpus of patient medical data records associated with the user.

4. The computer-implemented method of claim 1, wherein the encryption key is based on login credentials obtained when the network connection is available.

5. The computer-implemented method of claim 1, wherein the encrypted patient medical data record was symmetrically encrypted with the encryption key.

6. The computer-implemented method of claim 1, wherein the encrypting comprises:
symmetrically encrypting the offline-updated patient medical data record with the offline encryption key.

7. The computer-implemented method of claim 1, further comprising, when the network connection is offline:
creating a second offline-updated patient medical data record based on a new patient medical data record;
updating the offline-access record with information about the second offline-updated patient medical data record; and
encrypting and storing the second offline-updated patient medical data record and the updated offline-access record locally.

8. The computer-implemented method of claim 1, wherein the offline-access record comprises at least one of: a type of patient medical data record access including at least one of selecting, viewing, creating, modifying, or deleting a patient medical data record; information identifying the offline-updated patient medical data record accessed; an identification of the user who accessed the offline-updated patient medical data record; a date and time of access; or a content added, modified, or deleted during the access.

9. The computer-implemented method of claim 1 for resolving a collision among two or more offline-updated medical data records, comprising:
receiving a confirmation request to update a corresponding patient medical data record, wherein the confirmation request includes at least one of: a date and time of each of the two or more offline-updated patient medical data records is created, an identity of each user associated each of the two or more offline-updated medical data records, a patient associated with the two or more offline-updated patient medical data records, or a content added, modified, or deleted in each of the two or more offline-updated medical data records; and
sending a confirmation response to update or cancel the update.

10. A non-transitory computer readable storage medium embodying a program of instructions executable by at least one processor located on a client device to perform operations for offline EHR management, the operations comprising:
receiving, by a client device, via a network connection, an encryption key and an encrypted patient medical data record corresponding to the encryption key;
storing, by the client device, the encryption key and the encrypted patient medical data record in a browser application cache;
when the client device determines that the network connection is offline:
   accessing an application in the browser application cache;
   presenting, to a user, a login through the application;
   receiving login credentials from the user;
   generating an offline encryption key based on the login credentials;
   comparing the offline encryption key to the encryption key stored in the browser application cache;
   determining that the offline encryption key matches the encryption key; and
   in response to the offline encryption key matching the encryption key:
     accessing the encrypted patient medical data record stored in the browser application cache;
     decrypting the encrypted patient medical data record with the offline encryption key;
     creating an offline-updated patient medical data record based on the decrypted patient medical data record;
     creating an offline-access record based on the offline-updated patient medical data record; and
     encrypting and storing the offline-updated patient medical data record and the offline-access record locally in the browser application cache using the offline encryption key; and when the client device determines that the network connection is available:

receiving, from a server, a request for an offline-access record and an offline-updated patient medical data record; and transmitting, to the server, the encrypted offline-access record and the encrypted offline-updated patient medical data record from the browser application cache.

11. The non-transitory computer readable storage medium of claim 10, the operations further comprising, prior to the client determining that the network connection is offline:
receiving, from the server, the application; and
locally storing, by the client device, the received application in the browser application cache.

12. The non-transitory computer readable storage medium of claim 10, wherein the encrypted patient medical data record received from the server constitutes a filtered subset of a corpus of patient medical data records associated with the user.

13. The non-transitory computer readable storage medium of claim 10, wherein the encryption key is based on login obtained when the network connection is available credentials.

14. The non-transitory computer readable storage medium of claim 10, wherein the offline-access record comprises at least one of: a type of patient medical data record access including at least one of selecting, viewing, creating, modifying, or deleting a patient medical data record; information identifying the offline-updated patient medical data record accessed; an identification of the user who accessed the offline-updated patient medical data record; a date and time of access; or a content added, modified, or deleted during the access.

15. The non-transitory computer readable storage medium of claim 10, for resolving a collision among two or more offline-updated medical data records, comprising:
receiving a confirmation request to update a corresponding patient medical data record, wherein the confirmation request includes at least one of: a date and time of each of the two or more offline-updated patient medical data records is created, an identity of each user associated each of the two or more offline-updated medical data records, a patient associated with the two or more offline-updated patient medical data records, or a content added, modified, or deleted in each of the two or more offline-updated medical data records; and
sending a confirmation response to update or cancel the update.

16. A system for offline EHR management, comprising:
one or more processors executing on a client device;
a memory located on the client device coupled to the one or more processors, and which includes a browser application cache;
an application stored in the browser application cache, executed by the one or more processors; and
a network interface,
wherein the one or more processors are configured to:
receive, by the client device, via a network connection, an encryption key and an encrypted patient medical data record corresponding to the encryption key;
store, by the client device, the encryption key and the patient medical data record in a browser application cache;
when the client device determines that the network connection is offline:
present, to a user, a login through the application;
receive login credentials from the user;
generate an offline encryption key based on the login credentials;
compare the offline encryption key to the encryption key stored in the browser application cache; and
determine that the offline encryption key matches the encryption key:
accessing the encrypted patient medical data record stored in the browser application cache;
decrypting the encrypted patient medical data record with the offline encryption key;
creating an offline-updated patient medical data record based on the decrypted patient medical data record;
creating an offline-access record based on the offline-updated patient medical data record; and
encrypting and storing the offline-updated patient medical data record and the offline-access record locally in the browser application cache using the offline encryption key; and
when the client device determines that the network connection is available:
receiving, from a server, a request for an offline-access record and an offline-updated patient medical data record; and
transmitting, to the server by the network interface, the encrypted offline-access record and the encrypted offline-updated patient medical data record from the browser application cache.

17. The system of claim 16, wherein the encrypted patient medical data record received from the server constitutes a filtered subset of a corpus of patient medical data records associated with the user.

18. The system of claim 16, wherein the offline-access record comprises at least one of: a type of patient medical data record access including at least one of selecting, viewing, creating, modifying, or deleting a patient medical data record; information identifying the offline-updated patient medical data record accessed; an identification of the user who accessed the offline-updated patient medical data record; a date and time of access; or a content added, modified, or deleted during the access.

19. The system of claim 16, for resolving a collision among two or more offline-updated medical data records, the one or more processors configured to:
receive a confirmation request to update a corresponding patient medical data record, wherein the confirmation request includes at least one of: a date and time of each of the two or more offline-updated patient medical data records is created, an identity of each user associated each of the two or more offline-updated medical data records, a patient associated with the two or more offline-updated patient medical data records, or a content added, modified, or deleted in each of the two or more offline-updated medical data records; and
send a confirmation response to update or cancel the update.

20. The system of claim 16, further comprising, when the network connection is offline, the one or more processors are configured to:
create a second offline-updated patient medical data record based on a new patient medical data record;
update the offline-access record with information about the second offline-updated patient medical data record; and encrypt and store the second offline-updated patient medical data record and the updated offline-access record locally.

\* \* \* \* \*